(12) United States Patent
Shibata et al.

(10) Patent No.: US 6,284,734 B1
(45) Date of Patent: Sep. 4, 2001

(54) INHIBITORS AGAINST PROSTATE-SPECIFIC ANTIGEN

(75) Inventors: Kozue Shibata; Jun-ichi Kajihara, both of Kobe; Kazuyuki Hirano, Gifu, all of (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 0 days.

(21) Appl. No.: 09/161,421

(22) Filed: Sep. 24, 1998

(30) Foreign Application Priority Data

Sep. 24, 1997 (JP) .................................................. 9-278190

(51) Int. Cl.[7] .............................. C07K 7/06; A61K 38/08
(52) U.S. Cl. ............................ 514/15; 530/324; 530/325; 530/326; 530/327; 514/15
(58) Field of Search ..................................... 530/328, 327, 530/326, 325, 324; 514/15

(56) References Cited

U.S. PATENT DOCUMENTS 5,569,742 * 10/1996 Kirby et al. ........................... 530/317
5,854,206 * 12/1998 Twardzik et al. ...................... 514/12

OTHER PUBLICATIONS

Ngo et al., 'Computational Complexity, Potein Structure Prediction, and the Levinthal Paradox,' The Protein Folding Problem and Tertiary Structuer Prediction. Ed. K. Merz and L. Le Grand. BirkHauser, Boston MA. pp. 491–495, 1994.*

Rudinger, J. (1976). Peptide Hormones (ed. J.A. Parsons). University Park Press. Baltimore. pp 1–7, 1976.*

Fowlkes et al. 'Characterization of Glycosaminoglycan Binding Domains Present in Insulin Like Growth Factor Binding Protein 3', J. Biol. Chem. vol. 271, 25, pp. 14676–14679, 1996.*

* cited by examiner

Primary Examiner—Christopher S. F. Low
Assistant Examiner—Anish Gupta
(74) Attorney, Agent, or Firm—Jacobson Holman, PLLC

(57) ABSTRACT

According to the present invention, there are provided inhibitors against prostate-specific antigen which comprise as a minimum unit a peptide consisting of Gly-Phe-Tyr-Lys-Lys-Lys-Gln-Ser-Arg, and such inhibitors can be expected to constitute a therapeutic drug against prostate carcinoma and prostate hyperplasia.

2 Claims, No Drawings

INHIBITORS AGAINST PROSTATE-SPECIFIC ANTIGEN

The present invention relates to inhibitors against prostate-specific antigen.

BACKGROUND OF THE INVENTION

Human prostate-specific antigen essentially has been well known as a diagnostic marker in blood for patients with prostate carcinoma or hyperplasia, but recently, there has been advocated a new theory that human prostate-specific antigen acts to degrade specifically IGF (insulin-like growth factor) binding protein 3 to thereby cause increases in TGF levels in the prostate tissue, resulting in onset or progression of prostate carcinoma or development of prostate hyperplasia.

Accordingly, there exist great expectations that a drug being capable of inhibiting the said antigen would be effective in the treatment of prostate carcinoma and prostate hyperplasia.

Prostate-specific antigen (hereinafter referred to briefly as "PSA") was isolated in the form of γ-seminoprotein from human seminal plasma by Hara et al. in 1971 (Jp. J. Legal Med., 25: 322, 1971), and was thereafter found to be identical to a substance purified from the prostate tissue by Wang et al., while the said antigen was also observed to be expressed specifically in the prostate (Invest. Urol., 17: 159–163, 1979 and Oncology, 99: 1, 1982), thus leading i-o establishment of the unified appellation "prostate-specific antigen". And Wang et al. discovered that patients with prostate hyperplasia or carcinoma show a raised blood level of PSA (Prostate, 2: 89–95, 1981), and currently, PSA has been put in wide use as a diagnostic marker in blood for such diseases.

PSA was long left unclassified for most of its actions in the living body, but Watt et al. determined its complete amino acid sequence and demonstrated that PSA is a protease of the kallikrein family which belongs to a kind of serine proteases (Proc. Natl. Acad. Sci. USA, 88: 3166–3170, 1986), They also clarified that PSA exhibits chymotrypsin activity.

Recently, Cohen et al. and Lee et al. found that the substrate in the living body for PSA is IGF binding protein 3 (J. Endocrinol., 142: 407–415, 1994, and J. Clin. Endocrinol, Metab., 7 1367–1372, 1994), and from this finding, it has come to be inferred that when rises in PSA levels in the prostate tissue is brought about by prostate carcinoma, etc., there takes place selective degradation of IGF binding protein 3, with the resultant increases in free IGF levels, which in turn may induce diseases, such as prostate carcinoma and prostate hyperplasia. When it is feasible to inhibit the protease activity of PSA, accordingly, this would offer a possibility for providing a therapeutic drug for prostate carcinoma, prostate hyperplasia, etc., but such attempt has never been made so far in the past.

In recent years, the number of patients with prostate carcinoma or prostate hyperplasia has been on an increasingly upward trend, and in view of the fact that there has been no effective therapeutic drug available, the development of a highly specific drug without adverse effects is strongly demanded. Under these circumstances, the present inventors, taking the view that development of an inhibitor against PSA would be a means for achieving the above-mentioned objective, decided to conduct investigation into the said PSA inhibitor.

As a result, the present. inventors determined the site where PSA cleavages IGF bidning protein 3 and subsequently carried out intensive research on amino acid sequences surrounding such cleavage site, and these led to the finding that a peptide consisting of Gly-Phe-Tyr-Lys-Lys-Lys-Gln-Ser-Arq elicits inhibitory activity against PSA, resulting in establishment of this research work and completion of the present invention.

SUMMARY OF THE INVENTION

Namely, the present invention relates to PSA inhibitors which contain as a minimum unit a peptide consisting of Gly-Phe-Tyr-Lys-Lys-Lys-Gln-Ser-Arg.

DETAILED DESCRIPTION OF THE INVENTION

Using PSA as purified from human urine or seminal plasma, the present inventors identified the cleavage site for recombinant human IGF binding protein 3 (hereinafter referred to briefly as "r-IGFBP3") utilized as a substrate by the following procedure: in the first place, 50 μg of PSA and 20 μg of r-IGFBP3 were dissolved in 0.1M Tris hydrochloride buffer (pH 8.0), followed by reaction at 37° C. for 16 hrs.$_1$ and the reaction solution was subjected to reverse-phase HPLC to thereby fractionate peptide fragments split by PSA. Then, the fractionated peptide fragments were determined for their amino acid sequences, leading to the finding that cleavage took place at five sites of Arg97, Arg132, Lys198, Lys220 and Arg230. In order to give proved certainty to such consequence, the following peptide having the amino acid sequences vicinal to those of five cleavage sites, followed by investigation into PSA cleavage activities on such peptide fragments, with the result that PSA splits all of these fragments, and this finding made sure that the above five locations serve as the specific recognition and cleavage sites for PSA. In the experiment, the below-described peptides were used, while there was adopted the procedure which comprised dissolving 10 μg of PSA and 10 nmol each of the peptides in 0.1M Tris; hydrochloride buffer (pH 8.0), and allowing the reaction to proceed at 37° C. for 16 hrs., followed analysis by reverse-phase HPLC Peptide 1: val(88)-Asn-Ala-Ser-Ala-Val-Ser-Arg-Leu-Arg-Ala-Tyr-Leu-Leu-Pro(102);

Peptide 2: Val(127)-Ser-Ser-Thr-His-Arg-Val-Ser-Asp-Pro-Lys-Phe(138);

Peptide 3: Leu(194)-Asn-His-Leu-Lys-Phe-Leu-Asn-val-Leu(203);

Peptide 4: Gly(217)-Phe-Tyr-Lys-Lys-Lys-Gln-Ser-Arg (225); and

Peptide 5: Pro(226)-Ser-Lys-Gly-Arg-Lys-Arg-Gly-Phe-Met(235).

Then, investigation was conducted into whether or not these peptides act to inhibit the PSA activity. Using as the substrate for assaying the PSA. activity Pro-Phe-Arg-MCA (4-methylcoumarin amide) which is utilized in the assay of kallikrein, as is described in detail below in the Example, determination was made of the residual activities in the coexistence of each of the peptides, with the resultant finding that only Peptide 4 inhibited specifically the PSA activity and therefore would possibly act as a specific inhibitor against PSA.

Among the sites where PSA cleavages r-IGFBP3, the peptide moieties corresponding to Peptides 1 and 2 were previously reported by Fielder et al. (Growth Regulation, 1: 164–172, 1994), whereas the those corresponding to Peptides 3, 4 and 5 were for the first time discovered by the present inventors.

With particular reference to Peptide 4 consisting of 9 amino acid residues, the peptide derivatives generated by having two residues deleted from Peptide 4 orL the side of the N-terminus or the c-terminus showed fairly decreased inhibitory activity, thus suggesting that the said nine amino acid residues are essential for the inhibitory activity.

And PSA degrades r-IGFB3 into fragments, whereby its degradation process can be confirmed by means of SDS-electrophoresis and Western blotting. In the degradation reaction system, addition of Peptide 4 was found to suppress significantly the degradation of r-IGFEIP3, and this finding demonstrated that the said pepetide, by blocking the PSA activity, can actually suppress the degradation of r-IGFBP3.

Generally speaking, processed peptide preparations after administration to the living body often undergo degradation by peptidases, and in administering to patients the peptides according to the present invention, it is preferable to modify through acylation α-amino groups in the N-terminal amino acids, for example, with benzyloxycarbonyl (2), acetyl, t-butoxycarbonyl (Boc) and 9-tluorenylmethoxycarbonyl (Fmoc) groups or to amidate or esterify carboxyl groups in the C-terminal amino acids.

The present invention is to be furthermore illustrated below by way of examples, but is not understood to be limited by such examples.

EXAMPLE 1

Peptides 1 to 5 as mentioned in the above were prepared in a peptide synthesis device Type 432A synergy™ (Perkin Elmer Japan ; Applied Biosystems Co. of USA), and were thereafter determined and ascertained for their amino acid sequences with use of Protein Sequencer 476A (Perkin-Elmer Japan; Applied Biosystems Co. of USA). Taking Peptide 4 for example, the preparation procedure is to be described in the following;

The Device was equipped with a column packed with Fmoc-L-Arg (Pmc) resin (25 pmol) having a C-terminal amino acid of Arg immobilized thereon, and columns packed individually with different Fmoc amino acid derivatives (each 75 Aol), or Fmoc-L-Ser (tBu), Fmoc-L-Gln (Trt), Fmoz-L-Lys (Boc), Fmoc-L-Lys (Boc), Fmoc-L-Lys (Boc), Fmoc-L-Tyr (tBu), Fmoc-L-Phe and Fmoc-L-Gly, were arranged on the wheel of the Device in the above-mentioned order to conduct automatic synthesis. The peptide resin was placed in a 50-ml conical tube, followed by successive addition of 50 $\mu$l each of thioanisole and ethanedithiol and 900 $\mu$l of trifluoroacetic acid (TFA). The tube was closed and shaken slightly at a regular interval of 15 min. to allow the reaction to proceed for 1 hr at room temperature. After conclusion of the reaction, 15 ml of t-butyl methyl ether (MTBE) was added, and the solution mixture was shaken vigorously and filtered by suction. After washing several times with 10 ml of MTBE, the peptide remaining on the filter membrane was dissolved in 2N acetic acid, and the solution was filtered by suction. The recovered peptide was freeze-dried and subjected to a Cosmosil 5C18 column (produced by Nakarai Tesc Co. of Japan) equilibrated with 0.1% TFA, followed by elution with a linear-concentration gradient of acetonitrile. The thus prepared peptide was freeze-dried and the amino acid sequence was identified as Gly-Phe-Tyr-Lys-Lys-Lys-Gln-Ser-Arg by subjecting a portion of it to the above-mentioned automatic analyzer.

Peptides 1 to 3 and 5 were also synthesized automatically in the similar manner with use of their respectively corresponding Fmoc amino acid derivatives and their amino acid sequences were determined.

EXAMPLE 2

While using 0.1 $\mu$l of 100 $\mu$M or 10 $\mu$M Pro-Phe-Arg-MCA (supplied by Peptide Research. Institute of Japan) as a substrate, 0.1 ml of 100 $\mu$M of each of Peptides 1 to 5 was mixed with the substrate and 0.7 ml of 0.1M Tris-hydrochloride buffer (pH 8.0) to allow the reaction to proceed at 37° C. for 5 min, followed by addition of 0.1 ml of 0.12 mg/ml PSA solution. The reaction solution was subjected to time-course measurement of fluorescence intensity (Ex380 nm, Em460nm) at 37° C. for 3 min, and the inhibitory activity value was determined from a slope of the straight line. Each of Peptides, which was found to exhibit inhibition, was admixed with 0.1 ml of 40 ng/ml kallikrein solution in place of PSA to carry out the experiment in a similar manner. In the above experiments, Pro-Phe-Arg-MCA, Peptides 1 to 5 PSA and kallikrein were used after being dissolved in 0.1M Tris-hydrochloride buffer (pH 8.0).

The experimental results are shown in Table 1; the columns A and B indicate the figures obtained in the case of addition of PSA, being split into those for an equimolar mixture of the substrate Pro-Phe-Arg-MCA with each of Peptides (column A) and for a 1.10 molar ratio mixture of the substrate and each of Peptides (column B), respectively, with concentration-dependent inhibition of the PSA activity being noted only in the case of addition of Peptide 4, while the column C shows the results obtained in the case of addition of kallikrein, whereby the substrate and each Peptide were mixed at an equimolar ratio with the kallikrein activity being suppressed by Peptide 4. These findings are in good agreement with the fact that PSA a protease belonging to the kallikrein family . Table 1:

TABLE 1

|  | A | B | C |
| --- | --- | --- | --- |
| Enzyme added | PSA | PSA | Kallikrein |
| Substrate:Pepetide (molar ratio) | 1:1 | 1:10 | 1:1 |
| Residual activity rate (%) after addition of Peptides: | | | |
| Peptide-1 | 107.4 | 100.7 | — |
| Peptide-2 | 87.5 | 104.8 | — |
| Peptide-3 | 83.5 | 73.3 | — |
| Peptide-4 | 66.5 | 46.6 | 44.1 |
| Peptide-5 | 75.1 | 84.8 | — |

Note; The residual activity rates were calculated on the basis of 100% taken without addition of any Peptide.

EXAMPLE 3

A specimen was prepared by dissolving 0.57 $\mu$g of PSA and 2.0 $\mu$g of r-IGFBP3 (manufactured by Upstate Co. of USA) in 0.1M Tris-hydrochloride buffer (pH 8.0), followed by reaction at 37° C. for 16 hrs, while another specimen was prepared by dissolving 0.57 $\mu$g of PSA, 2.0 $\mu$g of r-TGFBP3 (manufactured by Upstate Co. of USA) and 4 nmol of Peptide 4 in 0.1M Tris-hydrochloride buffer (pH 8.0), followed by reaction at 37° C. for 16 hrs. Each of the specimens was subjected to a 4 to 20% gradient gel to conduct SDS electrophoresis under non-reduction in the conditions described by Laemmli et al. (Iqature, 227: 680–685, 1970). After electrophoresis, separated proteins were transferred to a nitrocellulose membrane to carry out Western blotting using anti-IGFBP3 antibody (produced by Biogenesis Co. of USA) as a primary antibody and anti-rabbit antibody (produced by Promega Co. of USA) labeled with horseradish peroxidase (HRP) as a secondary antibody. The HRP activity was detected by chemiluminescence (Renaissance Western Blot Chemiluminescence Reagent, NEN™ produced by Life Science Products Co. of USA), and the protein bands as detected were quantitatively determined by use of a densitometer.

Table 2 shows the results, in which surface-area measurement was made of the band detected at 50 kDa for each of the specimens on the assumption that the band at 50 kDa in molecular weight as detected in the electrophoresis with r-IGFBP3 alone was to be a unresolved band. The residual rate of the 50 kDa band in each specimen was calculated relative to the surface area determined when r-IGFBP3 alone was electrophoresed, thereby revealing that the presence of added Peptide 4 resulted in ca. 30% suppression against degradation of r-IGFBP3, as compared with the absence of Peptide 4. This demonstrated that Peptide 4, through suppression of the PSA activity, can suppress degradation of r-IGFBP3.

TABLE 2

|  | Surface area of the 50 kDa band | Residual rate % | Degradation suppression rate, % |
|---|---|---|---|
| r-IGFBP3 alone | 29.8 | 100.0 | — |
| r-IGFBP3 + PSA | 14.9 | 50.0 | — |
| r-IGFBP3 + PSA + Peptide 4 | 19.4 | 65.1 | 30.2 |

What is claimed is:

1. An isolated peptide exhibiting inhibitory activity against prostate specific antigen, which peptide comprises the formula (SEQ ID NO: 1):

Gly-Phe-Tyr-Lys-Lys-Lys-Gln-Ser-Arg.

2. The isolated peptide as claimed in claim 1, wherein the C-terminus is amidated or esterified and/or the N-terminus is acylated.

* * * * *